United States Patent
Day et al.

[19]

[11] Patent Number: 5,876,204
[45] Date of Patent: Mar. 2, 1999

[54] DENTAL IMPLANT POSITIONING GUIDE

[75] Inventors: Thomas H. Day, San Diego; Robert L. Riley; Kermit Stott, both of Vista, all of Calif.

[73] Assignee: Sulzer Calcitek Inc., Carlsbad, Calif.

[21] Appl. No.: 978,069

[22] Filed: Nov. 25, 1997

[51] Int. Cl.⁶ ........................................... A61C 8/00
[52] U.S. Cl. ............................................ 433/173; 433/72
[58] Field of Search .................................. 433/173, 174, 433/175, 201.1, 72, 75, 76

[56] References Cited

U.S. PATENT DOCUMENTS

| | | | |
|---|---|---|---|
| 1,216,596 | 2/1917 | Nishi | 433/75 |
| 3,468,027 | 9/1969 | Dobranski et al. | 32/1 |
| 4,479,780 | 10/1984 | Gores | 433/74 |
| 4,683,875 | 8/1987 | Rabinowitz | 128/62 |
| 4,768,953 | 9/1988 | Nestor et al. | 433/72 |
| 4,842,518 | 6/1989 | Linkow et al. | 433/174 |
| 4,907,969 | 3/1990 | Ward | 433/173 |
| 4,932,868 | 6/1990 | Linkow et al. | 433/174 |
| 4,934,935 | 6/1990 | Edwards | 433/174 |
| 4,964,861 | 10/1990 | Agee et al. | 606/87 |
| 5,007,835 | 4/1991 | Valen | 433/174 |
| 5,087,197 | 2/1992 | Sullivan | 433/74 |
| 5,219,286 | 6/1993 | Hader | 433/172 |
| 5,350,301 | 9/1994 | De Buck | 433/173 |
| 5,564,922 | 10/1996 | Rosa et al. | 433/173 |
| 5,607,305 | 3/1997 | Anderson et al. | 433/223 |
| 5,695,344 | 12/1997 | Blacklock et al. | 433/213 |

*Primary Examiner*—John J. Wilson
*Attorney, Agent, or Firm*—Philip S. Lyren

[57] ABSTRACT

A dental positioning guide has two pins connected to a hub section. The pins may be rotated to a plurality of angular positions.

49 Claims, 4 Drawing Sheets

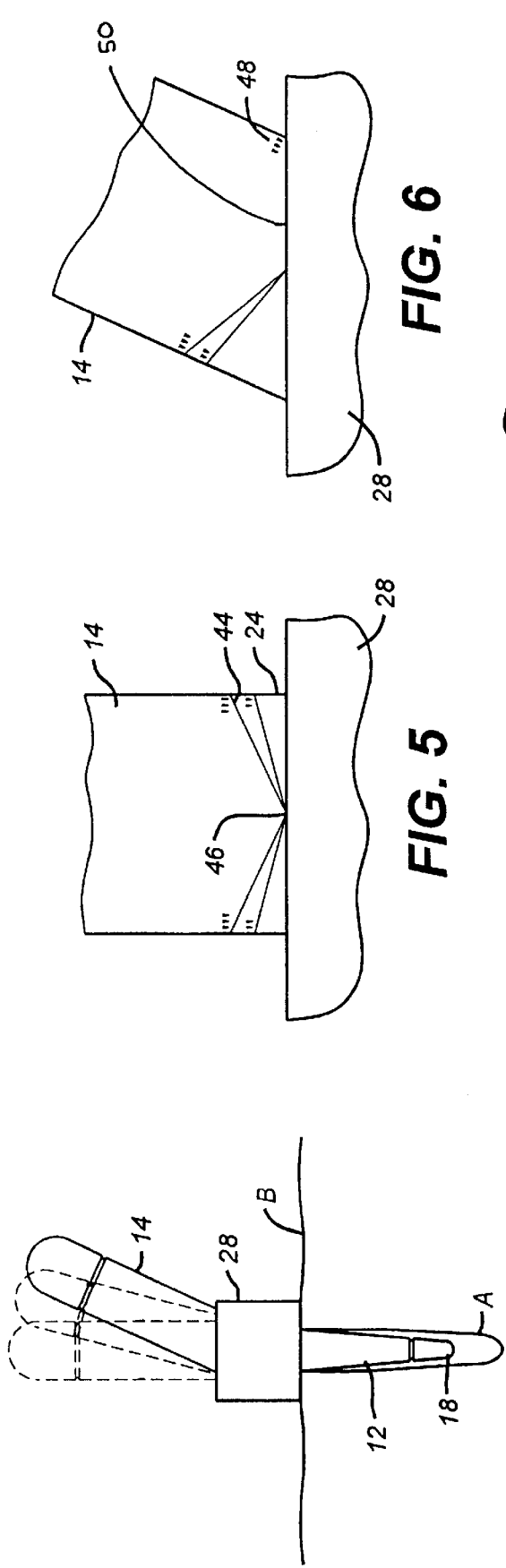

DENTAL IMPLANT POSITIONING GUIDE

BACKGROUND OF THE INVENTION

This invention relates generally to positioning guides for dental implants, and to techniques for locating the placement of dental implants. The positioning guides may also be called parallel pins, placement guides, angulation indicators, dental guides and surgical guides.

People who are lacking an entire tooth and root structure for one or more teeth may receive prosthetic replacements. These replacements may include an implant that is surgically secured to the jawbone. An abutment may engage the implant and extend above the gum or gingival tissue. A natural looking artificial tooth crown may then be secured to the abutment. In many cases, the prosthetic device is indistinguishable from a natural tooth. In this way, people who are edentulous (for example, because they have lost the entire tooth structure) can receive one or more prosthetic replacements.

It may not always be possible to position the implant and the prosthetic tooth in precise vertical alignment. This inability to achieve a vertical orientation can occur for a number of reasons. Most obviously, the patient's natural teeth may not permit such a vertically aligned orientation. Of course, the prosthetic replacement must align with the existing angulation of the natural teeth.

In addition, the surgeon may forced to position the implant in the jaw at an angle to a precise vertical orientation. Among the reasons for deliberate angularity are anatomical considerations relating to the volume and quality of the jawbone tissue, as well as the loss of necessary bone support. Thus, the implantologist, in a variety of circumstances may use a range of implant angulations of both the supragingivally extending portion of the prosthetic replacement as well as the portion extending into the bone itself.

The implant procedure initially involves making an incision in the gum tissue to expose the underlying bone.

Next, a initial hole is drilled into the bone to a depth less than the length of the implant. The initial hole diameter is generally significantly smaller in diameter than the ultimate implant diameter. This diameter however, is enlarged during the surgical procedure as successive drilling steps occur. Each step typically includes drilling the hole with a larger diameter drill. This diameter difference allows the implantologist to adjust the final angulation of the implant hole in the bone. The adjustment enables the implantologist to properly orientate the implant and the external prosthetic replacement.

During the surgical procedure, the implantologist commonly uses what is known as a parallel pin or positioning guide to determine the correct orientation of the holes drilled into the bone. The parallel pin includes a pair of pins of different diameters extending outwardly from a transversely oriented annular stop. One of the pins, sized to the initial hole diameter, is inserted into the initial hole until the stop rests on the bone crest. The implantologist can observe the orientation of the supragingivally extending portion of the parallel pin and determine the angle of the hole. If the implantologist determines that the angulation is inappropriate, some adjustment of the hole is still possible as the angulation is adjusted during subsequent drilling steps.

The implantologist must also orient the initial holes for other prosthetic replacements relative to the initial hole already formed. The implantologist commonly uses an implant template which has been prepared in advance to facilitate the placement of other initial holes relative to the first formed hole. The template, for example, will show the correct spacing between adjacent holes.

After the initial hole is drilled, additional drills enlarge the size of the hole. During an intermediate stage of drilling, the second end of the parallel pin is inserted into the intermediate sized hole. The second end has a larger diameter than the first end and, like the first end, is used to depict the angulation of the hole. If the orientation is correct, the final hole is drilled.

The implantologist may have a set of parallel pins, and each parallel pin may have one of a variety of different angles. For example, parallel pins with angles of 0°, 15° and 25° may be stocked for a variety of different types of implants and abutment systems. These angled parallel pins may then be utilized in the fashion described above to determine if the correct hole angulation has been achieved. Further, the angled parallel pins may also be utilized with pre-angled abutments.

During an implantation procedure, the implantologist carefully positions implants to have sufficient spacing between adjacent implants and teeth. Generally, for example, the minimum edge-to-edge spacing between adjacent implants is approximately 4 to 6 millimeters; and the minimum spacing between an implant and a natural tooth is about 3 millimeters. Correct spacing is desired to reduce and evenly distribute occlusal forces. In order to accurately position the implants, the implantologist may use an acrylic template or surgical stent.

One disadvantage associated with prior implant system is that an inventory of numerous parallel pins is required. An implantologist, for example, must have a separate parallel pin for each different degree of angulation, such as separate pins for 0°, 10°, 15°, 20°, 25° and 30°. The separate pins are costly to the implantologist and require storage space in a surgical kit.

Another disadvantage with prior implant systems is a separate template or surgical stent is required to correctly position implants to adjacent teeth and other implants. These devices are costly and may also require separate storage space in the surgical field.

As another disadvantage, prior art parallel pins are not designed to determine the fit of components of the prosthetic attachment system, such as an abutment. A separate device may be used for such measurements and indications.

SUMMARY OF THE INVENTION

The present invention is directed toward a multi-purpose positioning guide. The positioning guide includes two pins extending from a hub region. A first pin is adapted to fit into the initial hole drilled into the bone. A second pin is adapted to extend supragingivally. In certain embodiments, a pivotal connection is provided between the first and second pins. In one embodiment, the second pin may be adjusted to one of a plurality of fixed angular positions relative to the first pin. The second pin may be rotated to extend generally parallel to the surface of the jaw line.

The present invention is also directed toward a method of determining the correct location for dental implants to be implanted in the jaw bone. This method includes the step of positioning one pin of a positioning guide in a hole formed in the jaw bone. A second pin extends supragingivally, and the angle of this pin may be adjusted to one of a series of selectable orientations. The second pin also may be adjusted to operate as a spacing guide to determine the correct spacing between a hole in the jaw bone and an adjacent tooth, hole, implant, or possible location for a tooth, hole, or implant.

One advantage with present invention is that the pins of the positioning guide are adjustable to various angles. Several separate parallel pins each fixed at different degrees of angulation are no longer needed. The storage space and cost of manufacture are significantly reduced.

As another advantage, a separate template or surgical stent is not required to correctly position implants to adjacent teeth and other implants. The pins of the positioning guide include a mark that determines the correct location for adjacent teeth and implants.

As another advantage, the positioning guide is able to determine whether sufficient space exists around the coronal end of the implant to accommodate components of the prosthetic attachment system, such as an abutment. The positioning guide includes a hub that is sized to represent the placement of such a component.

The details of one or embodiments of the invention are set forth in the accompanying drawing and the description below. Other features, objects and advantages of the invention will be apparent from the description and drawings, and from the claims.

BRIEF DESCRIPTION OF THE DRAWING

FIG. 4 is a schematic view showing the angular positions in accordance with one embodiment of the present invention;

FIG. 5 is a partial, greatly enlarged front elevational view of the embodiment shown in FIG. 1 showing the angle indicator;

FIG. 6 is a partial, greatly enlarged front elevational view showing the angle indicator with an angled intermediate pin;

FIG. 7 illustrates the embodiment shown in FIG. 1 in position with an angled initial hole;

FIG. 8 shows the embodiment of FIG. 1 in use as a guide for an adjacent initial hole;

DETAILED DESCRIPTION OF PREFERRED EMBODIMENTS

Figure 1:
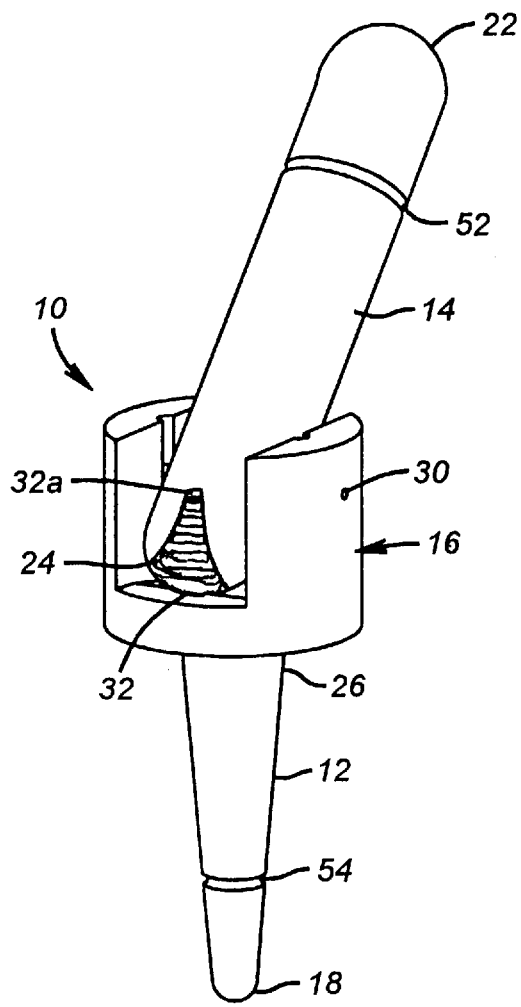
FIG. 1 is an enlarged perspective view of one embodiment of the present invention.

Referring to the drawing wherein like reference characters are used for like parts throughout the several views, a positioning guide 10 includes an initial hole pin 12 and an intermediate hole pin 14 connected by a hub or pivot connection 16. The initial hole pin 12 may be sized and shaped to be received in a particular diameter of initial hole and may extend from a relatively narrow distal end 18 to a relatively wider proximal end 26 connected to the pivot 16. The intermediate hole pin 14 may be of relatively uniform cross-sectional diameter, having a rounded distal end 22 and a proximal end 24. The diameter of the intermediate hole pin 14 may correspond generally to the intermediate hole in the bone.

Figure 2:
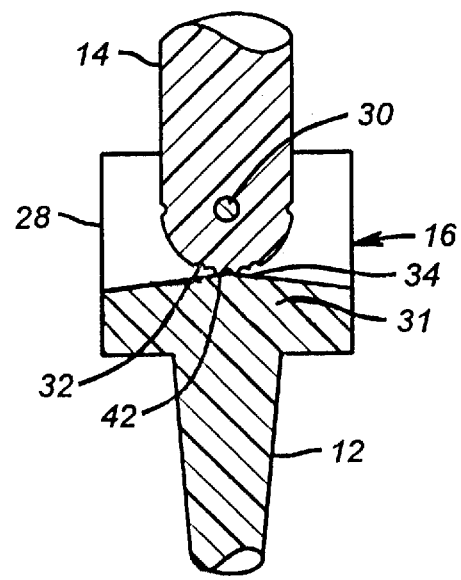
FIG. 2 is an enlarged, partial vertical cross-sectional view of the embodiment shown in FIG. 1.

As shown in FIG. 2, the pivot 16 may include a ridge or detent portion 31, a housing 28 and a pivot pin 30. The distal end 24 of the intermediate hole pin 14 may include a series of angularly spaced depressions or ridges 32 arranged to be engaged by the apex 34 of the detent portion 31. In this way, as the intermediate pin 14 is rotated relative to the pivot 16, the apex 34 serially engages the set of angularly spaced depressions 32. Advantageously, the depressions 32 may be arranged on a common radius with respect to the pivot pin 30. In this way, the initial hole pin 12 and intermediate hole pin 14 may be selectively oriented at one of a variety of pre-determined angular orientations with respect to one another. Depressions 32 may also be absent and enable distal end 24 to frictionally engage detent portion 31.

Figure 3:
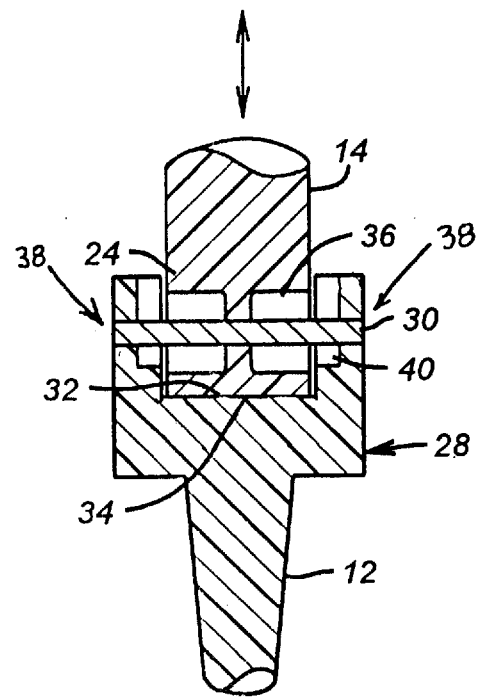
FIG. 3 is an enlarged, vertical cross-sectional view of the embodiment shown in FIG. 2.

Pivot pin 30 may be made to be somewhat flexible. Looking to FIG. 3, it is possible to use resilient engagement to maintain the position of the apex 34 with respect to a desired depression 32. While those skilled in the art will appreciate that the provision of a resilient bias between these contacting surfaces may be achieved in a variety of ways, a resilient wire may act as the wire pivot pin 30. This wire extends through an oversized opening 36 in the proximal end 24 of the intermediate hole pin 14. The oversized opening 36 allows the pivot pin 30 to flex relative to the intermediate pin 14 and to use the natural resiliency of the pivot pin 30 to retain the pin 14 against the detent portion 31, as indicated by the arrows in FIG. 3.

The pivot pin 30 may be fixed in the housing 28 in a pair of opposed openings 38. The surrounding portion 40 of the housing 28 may also be removed to allow free motion of the pivot pin 30.

With the initial hole pin 12 in an initial hole A, as shown in FIG. 4, the housing 28 may rest on bone B. The initial hole A may in fact have a vertical extension greater than the length of the initial pin 12 so that the distal end 18 of the pin 12 is spaced above the end of the hole A. In this position, the intermediate hole pin 14 may be rotated through a series of preset angular positions. In one embodiment, each of the depressions 32 (shown in FIG. 1) corresponds to an intermediate hole pin 14 angular orientation of 0°, 15° and 25° relative to the initial hole pin 12. More depressions could also be used and correspond to various angular orientations, such as 0°, 5°, 10°, 15°, 20°, 25°, 30°, or more. Thus, the implantologist can rotate the intermediate hole pin 14 to one of a plurality of angles to visualize the desired orientation and its affect on adjacent structures. The intermediate hole pin 14 stays in the desired position, until displaced to a different position by the implantologist, through the resilient engagement between the detent portion 31 and a depression 32.

As shown in FIG. 5, the various available angular orientations can be inscribed in the form of lines 44 extending from a central point 46 on the proximal end 24 of the intermediate hole pin 14. When the pin 14 is rotated, an angle indicator 48 is oriented just above the upper surface 50 of the housing 28, as indicated in FIG. 6. This allows the implantologist to readily confirm the orientation. The angle of pin 12 with respect to pin 14 gives the implantologist the necessary angle to correctly choose an abutment or attachment system for the prosthesis.

In addition, an angularly oriented initial hole A may be engaged by the initial hole pin 12, as shown in FIG. 7. In this case, the angulation of the pin 14 provides a vertical orientation. In addition, a nonvertical orientation could be achieved as well.

The positioning guide 10 may also be useful in locating the initial holes for adjacent implants, as shown in FIG. 8. Pin 14 includes a visually perceivable indicia 52. This indicia is shown as a groove but may have any one of various forms known to those skilled in the art, such as a color band, dot, line, hole, letter, number, mark, or the like. The distance from the proximal end of the pin to the indicia may vary. Preferably, the indicia is located approximately 3 to 8 millimeters from the proximal end. With the intermediate hole pin 14 rotated approximately 90° to an orientation generally parallel to the jaw line, indicated as B in FIG. 8, the mark 52 locates the next adjacent initial hole. As a result, the implantologist is able to easily visualize the minimum distance from the initial hole A to the location of the next initial hole to be drilled, because the distance is predetermined by the mark 52. The implantologist can then readily locate the necessary hole location. Since a similar mark 54 is also provided on the initial hole pin 12, similar confirmation can be made after the intermediate hole has been formed using the mark 54 of the initial hole pin 12.

Thus, the positioning guide 10 may provide a number of useful tools for the implantologist. In particular, the need to have a variety of different positioning guides or parallel pins at different angulations can be eliminated with certain embodiments of the present invention. This facilitates the "in place" examination of pin angulation without the need to try a variety of different pins. The orientation of the pins relative to one another can be indicated by marks on the pins. In addition, the angularly displaceable pin portions may be utilized as an easy way to measure or indicate the necessary spacing between adjacent initial holes. This measuring capability facilitates the relatively awkward measurement of the distance between an initial hole and the adjacent implant initial hole site since the position of one end of the measuring tool is readily fixed by the engagement between the pin and the previously drilled initial hole. Thus, it can be appreciated that with one tool, the implantologist can easily make a variety of determinations.

Another advantage of the positioning guide is that the pivot may be sized or configured to verify that sufficient spacing exists between the implanted prosthesis and adjacent structures, such as natural teeth or other prosthesis.

During a typical dental implantation procedures, a hole is drilled into the jaw bone and the implant is positioned in the hole. During the next several months, the implant integrates with surrounding bone. After this time period, various prosthetic components may be attached to the implant. For example, an abutment may be connected to the top of the implant. An artificial tooth is then connected to the abutment. Alternatively, a coping with an artificial tooth may be attached directly to the implant. Regardless of the type of components attached to the implant, sufficient space must exist to accommodate the artificial tooth or prosthetic system.

Figure 9:
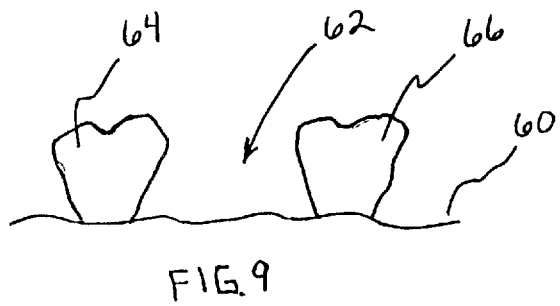
FIG. 9 shows a jaw bone requiring a single tooth restoration.
Figure 10:
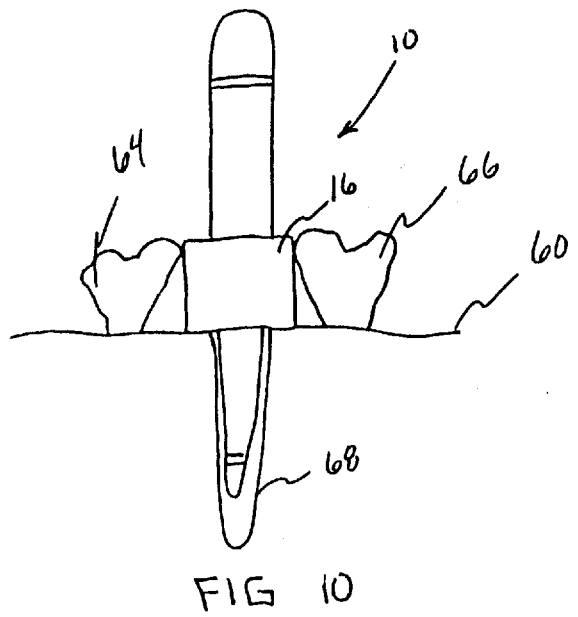
FIG. 10 shows the positioning guide of the present invention positioned between two teeth in FIG. 9.

FIG. 9 illustrates an example of a jaw bone requiring a single tooth restoration. In this figure, a jaw bone 60 has an edentulous region 62 located between two natural teeth 64 and 66. An artificial tooth will fit within this region between the teeth. During the implantation procedure, as noted, a hole 68 is drilled in jaw bone 60 between teeth 64 and 66, as shown in FIG. 10. If the hole is not properly centered or sufficient spacing does not exist between the two teeth, then the abutment or artificial tooth may not properly fit.

The pivot 16 of the positioning guide 10 may be sized or dimensioned to ensure the implant is positioned in the correct location and proper spacing exists for a prosthetic component. The pivot, for example, may have a size, width, shape, or the like to represent the placement of an abutment, artificial tooth, or tother prosthetic component. Preferably, the pivot has a diameter ranging from about 3 mm to about 7.5 mm.

After hole 68 is drilled into jaw bone 60, the positioning guide 10 is inserted into the hole. If the pivot 16 correctly fits between teeth 64 and 66, then the implantologist will know sufficient spacing exists for the placement of an abutment, tooth, or other component. Thus, the implantologist is able to verify at an early stage during the implantation procedure whether the hole is being drilled in the proper location and sufficient spacing exists.

Figure 11:
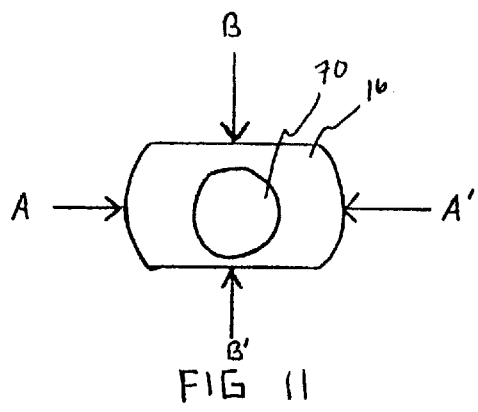
FIG. 11 shows an end view of an alternate embodiment of the positioning guide.
Figure 12:
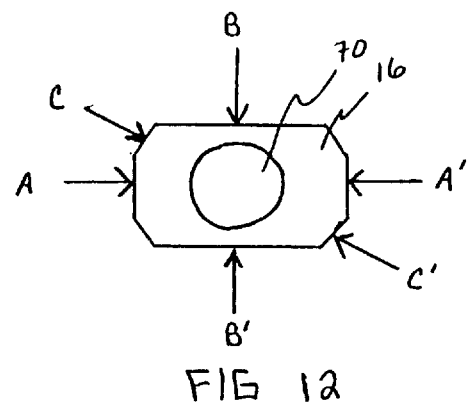
FIG. 12 shows an end view of another alternate embodiment of the positioning guide.

The pivot may have various shapes and sized to represent the placement of an abutment, tooth, or other component. Additionally, a single pivot may represent the placement of several components each having a different size. FIGS. 11 and 12 show an end view of pivot 16 and a pin 70. In FIG. 11, pivot 16 has two different dimensions, shown between A and A' and between B and B'. In FIG. 12, pivot 16 has a third dimension shown between C and C'. Each of these dimensions corresponds to the size of a different prosthetic component. During the implantation procedure, the positioning guide may be rotated between positions A–A', B–B', or C–C' to determine the available spacing.

Figure 13:
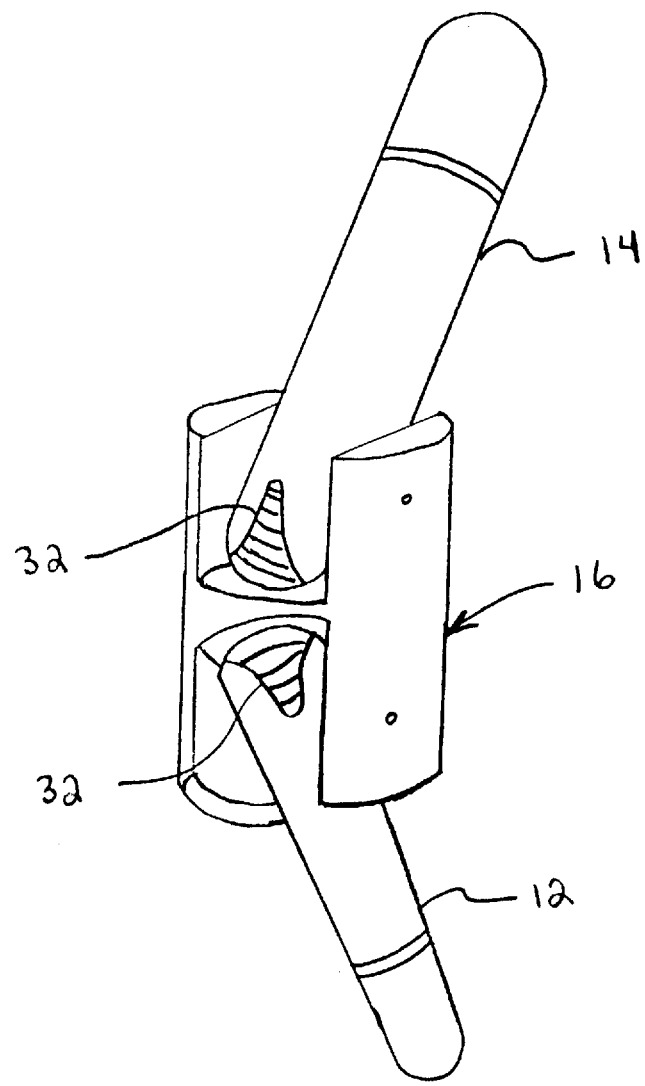
FIG. 13 shows a side view of yet another embodiment of the positioning guide.

FIG. 13 shows another embodiment for the positioning guide of the present invention. In this embodiment, both the pilot hole pin 12 and the intermediate hole pin 14 are rotatable with respect to hub 16. The distal end of pins 12 and 14 include a plurality of spaced ridges, detents, depressions, or the like (shown at 32) that engage a detent in the hub. Both pins may be rotated or pivoted about the hub and have a range of motion from −90° to 0° to +90°. The pins connect to the hub in a manner similar to the connection of pin 14 described in FIG. 1.

While the present invention has been described with respect to a limited number of preferred embodiments, those skilled in the art will appreciate numerous modifications and variations therefrom. The appended claims are intended to encompass all modifications and variations as fall within the true spirit and scope of the present invention.

What is claimed is:

1. A method for locating a position to place a dental implant into a second hole adjacent a first hole in a jawbone, comprising the steps of:

drilling said first hole into said jaw bone;

providing a positioning guide having a first pin with a visually perceivable indicia and a second pin;

positioning said second pin into said first hole;

adjusting the angle of said first pin with respect to said second pin;

using said indicia as a guide to locate said position to place said dental implant; and drilling said second hole at said position.

2. The method of claim 1 including the step of rotating said first pin until said indicia is adjacent said jaw bone.

3. The method of claim 1 in which said adjusting step includes rotating said first pin to a position approximately parallel to said jaw bone.

4. The method of claim 1 in which said adjusting step includes rotating said first pin between at least two stable positions.

5. The method of claim 1 in which said using step includes orienting said indicia adjacent said jaw bone.

6. The method of claim 1 including the step of rotating said first pin so said indicia is a distance from said first hole and adjacent said jaw bone.

7. The method of claim 6 in which said distance from said first hole gives said position to place said dental implant and drill said second hole.

8. The method of claim 1 including the steps of:
drilling said first hole to enlarge its diameter;
providing said positioning guide with another visually perceivable indicia on said second pin;
positioning said first pin into said first hole; and
adjusting the angle of said second pin with respect to said first pin.

9. The method of claim 8 including the step of rotating said second pin until said indicia on said second pin is adjacent said jaw bone.

10. The method of claim 9 including the step of viewing the location of said indicia to indicate said position to place said dental implant.

11. The method of claim 1 including the steps of:
removing said second pin from said first hole; and
positioning said first pin into said first hole.

12. The method of claim 1 including the steps of:
removing said second pin from said first hole;
enlarging said first hole;
placing said first pin into said enlarged first hole; and
adjusting the angle of said second pin with respect to said first pin.

13. A dental positioning guide, comprising:
a first pin;
a second pin; and a pivotal connection between said first and second pins in which said pivotal connection includes: a hub connected to a proximal end of said first pin and a proximal end of said second pin, and a pivot pin extending through said proximal end of said second pin.

14. The positioning guide of claim 13 in which:
said first pin is sized to fit into an initial hole drilled into a jaw bone; and
said second pin is sized to fit into a hole larger than said initial hole.

15. The positioning guide of claim 13 in which:
said first pin fits into a hole drilled into a jaw bone; and
said second pin extends supragingivally.

16. The positioning guide of claim 13 in which:
said first pin is smaller than said second pin; and
said second pin is rotatable to a plurality of angular positions with respect to said first pin.

17. The positioning guide of claim 13 in which said proximal end of said first pin is integrally formed with said pivotal connection.

18. The positioning guide of claim 13 in which said first pin includes a visually perceivable indicia.

19. The positioning guide of claim 18 in which said indicia is one of a mark, colored band, groove, dot, line, number, or letter.

20. The positioning guide of claim 18 in which said indicia is located at a distal end of said first pin.

21. The positioning guide of claim 13 further including visually perceivable indicia to indicate the relative angle between said first and second pins.

22. A method for determining a desired angle for a prosthetic attachment to be affixed to an implant implanted in a jaw bone, comprising the steps of:
drilling a hole into said jaw bone;
providing a positioning guide have two pins;
positioning one of said pins into said hole such that said other pin extends supragingivally from said jaw bone;
rotating said other pin to said desired angle;
removing said pin from said hole;
implanting said implant in said hole; and
providing an angled prosthetic attachment having an angular configuration equal to said desired angle.

23. The method of claim 22 in which said rotating step includes positioning said other pin at an angular orientation of 0°, 5°, 10°, 15°, 20°, or 25°.

24. The method of claim 22 including the step of affixing said angled prosthetic attachment to said implant.

25. A dental positioning guide, comprising:
a hub having first and second pins extending outwardly therefrom with said first pin being rotatable about said hub in which said hub has a diameter greater than the diameter of either said first and second pins.

26. The positioning guide, of claim 25 in which said first and second pins have different diameters.

27. The positioning guide of claim 26 in which:
said first pin has a diameter corresponding to a diameter of an intermediate hole drilled into a jaw bone; and
said second pin has a diameter corresponding to a diameter of an initial hole drilled into said jaw bone.

28. The positioning guide of claim 25 in which said first pin rotates to a plurality of stable angular orientations ranging from −90° to 0° to 90°.

29. The positioning guide of claim 25 in which said hub has a diameter corresponding approximately to the width of a natural tooth in a jaw bone.

30. The positioning guide of claim 25 in which said hub has a diameter equal to a prosthetic restoration.

31. The positioning guide of claim 25 in which said hub has a diameter ranging between approximately 3 millimeters to 7.5 millimeters.

32. A method for determining spacing between two teeth in a jaw bone, comprising the steps of:
drilling a hole into said jaw bone between said teeth;
providing a positioning guide having a hub with a width and a pin extending outwardly from said hub;
inserting said pin into said hole; and
comparing said spacing between said two teeth with said width of said hub.

33. A dental positioning guide, comprising:
a hub;
a first pin pivotally connected to said hub and having an elongated cylindrical configuration; and
a second pin pivotally connected to said hub and having an elongated tapered configuration.

34. The positioning guide of claim 33 in which said first and second pins are rotatably between −90° to 0° to 90° with respect to said hub.

35. The positioning guide of claim 33 in which:
said hub includes a housing forming a first opening between two oppositely disposed walls and a second opening between two other oppositely disposed walls;
said first pin has a proximal end that pivotally connects between said walls; and
said second pin has a proximal end that pivotally connects between said other walls.

36. A dental positioning guide, comprising:
a first pin;

a second pin;

a pivotal connection between said first and second pins;

said pivotal connection includes a ridge; and said second pin includes a series of spaced depressions that engage said ridge.

37. A dental positioning guide, comprising:

a first pin;

a second pin;

a pivotal connection between said first and second pins;

said pivotal connection includes a housing forming an opening between two oppositely disposed walls; and said second pin has a proximal end that fits within said opening between said walls.

38. The positioning guide of claim 37 in which said first pin has a proximal end connected to said housing.

39. The positioning guide of claim 37 in which a pivot pin extends through said proximal end and connects said second pin to said housing.

40. The positioning guide of claim 39 in which said second pin rotates about said pivot pin.

41. The positioning guide of claim 40 in which said proximal end moves through said opening.

42. A dental positioning guide, comprising:

a first pin;

a second pin;

a pivotal connection between said first and second pins; and said first pin includes a visually perceivable indicia located at a distal end of said first pin approximately 3 millimeters to 8 millimeters from a proximal end of said first pin.

43. A dental positioning guide, comprising:

a first pin;

a second pin;

a pivotal connection between said first and second pins; and said first pin and said second pin include a visually perceivable indicia.

44. A dental positioning guide, comprising:

a first pin having an elongated cylindrical configuration;

a second pin having an elongated tapered configuration; and a pivotal connection between said first and second pins.

45. A dental positioning guide, comprising:

a first pin;

a second pin;

a pivotal connection between said first and second pins;

said pivotal connection includes a first engaging means;

said first pin includes a second engaging means; and said first engaging means engages said second engaging means such that said first pin is rotatable to a plurality of different positions with respect to said second pin.

46. A dental positioning guide, comprising:

a first pin;

a second pin;

a pivotal connection between said first and second pins; and said pivotal connection includes a housing and a flexible pivot pin connecting said first pin to said housing.

47. A method for determining a desired angle for a prosthetic attachment to be affixed to an implant implanted in a jaw bone, comprising the steps of:

drilling a hole into said jaw bone;

providing a positioning guide having two pins and markings to indicate a relative angle between said two pins;

positioning one of said pins into said hole such that said other pin extends supragingivally from said jaw bone; and rotating said other pin to said desired angle.

48. The method of claim 47 including the step viewing said markings to determine said relative angle.

49. A dental positioning guide, comprising:

a hub having first and second pins extending outwardly therefrom with said first pin being rotatable about said hub and said first pin rotates to a plurality of stable angular orientations ranging from −90° to 0° to 90° and said positioning guide further includes indicia for indicating said angular orientations.

* * * * *